United States Patent [19]

Bryselbout et al.

[11] Patent Number: 5,152,176
[45] Date of Patent: Oct. 6, 1992

[54] PROCESS AND APPARATUS FOR DETERMINING THE QUALITY OF IMPURITIES IN A GAS BY CHROMATOGRAPHY IN GAS PHASE AND UTILIZATION FOR MEASURING THE QUANTITY OF DOPING IMPURITIES IN SILANE

[75] Inventors: Francis Bryselbout, Le Mesnil Saint Denis; Patrick Mauvais, Villepreux, both of France

[73] Assignee: L'Air Liquide, Societe Anonyme Pour l'Etude et l'Exploitation des Procedes, Paris, France

[21] Appl. No.: 587,185

[22] Filed: Sep. 24, 1990

[30] Foreign Application Priority Data

Sep. 22, 1989 [FR] France .................... 89 12447

[51] Int. Cl.⁵ ............... G01N 30/08; B01D 13/08
[52] U.S. Cl. .................... 73/23.41; 73/23.35; 73/23.42; 73/23.39; 55/197; 55/67; 422/89
[58] Field of Search ............ 73/23.35, 23.39, 23.4, 73/23.41, 23.42; 55/197, 386, 67; 422/89; 430/101

[56] References Cited

U.S. PATENT DOCUMENTS

| 3,168,823 | 2/1965 | Reinecke et al. | 73/23.39 X |
| 3,352,644 | 11/1967 | Lysj | 436/161 |
| 3,735,565 | 5/1973 | Gilby et al. | 55/197 |
| 3,897,211 | 7/1975 | Ririe, Jr. | 73/23.35 X |
| 4,180,389 | 12/1979 | Paul | 55/197 X |
| 4,234,315 | 11/1980 | Scott | 422/89 X |
| 4,454,043 | 6/1984 | Ting et al. | 210/659 |
| 4,992,083 | 2/1991 | Mueller et al. | 55/197 |

FOREIGN PATENT DOCUMENTS 2256702 7/1975 France .
2366564 4/1978 France .

OTHER PUBLICATIONS

Soviet Inventions Illustrated, Sep. 23, 1987, semaine 8737, abrege No. 87-262535/37, E37-J04-S03, Derwent Publications Ltd., Lonres, GB; & Su-A-12 86988 (Rezchikov V. G.) Jul. 12, 1984.

Primary Examiner—Hezron E. Williams
Assistant Examiner—Michael Brock
Attorney, Agent, or Firm—Browdy and Neimark

[57] ABSTRACT

The apparatus for determining the quantity of impurity in a gas by chromatography in gas phase comprises a device for cryogenically trapping impurities, which is provided with a column filled with granular particles of a product capable of adsorbing the impurities, refrigerating means capable of keeping the column at low temperature during passage of the gas loaded with impurities and reheating means for an ulterior desorption;
a first chromatographic adsorber in gas phase intended for a preliminary analysis and provided with a filling column for each impurity;
a device for the cryogenic recentering of the purities, which is provided with a capillary column, refrigerating means capable of keeping the column at low temperature during the passage of a carrier gas which has gone through the first chromatographic adsorber, and desorption reheating means;
and a second chromatographic adsorber in gas phase provided with a capillary column, a detection device being mounted at the outlet.

7 Claims, 4 Drawing Sheets

PROCESS AND APPARATUS FOR DETERMINING THE QUALITY OF IMPURITIES IN A GAS BY CHROMATOGRAPHY IN GAS PHASE AND UTILIZATION FOR MEASURING THE QUANTITY OF DOPING IMPURITIES IN SILANE

BACKGROUND OF THE INVENTION (a) Field of the Invention

The present invention is concerned with a process and a device for determining the quantity of impurities in a gas by chromatography in gas phase and the utilization of such a process for measuring the quantity of doping impurities found in traces in silane.

(b) Description of Prior Art

The technology of chromatography, under normal conditions, does not permit detection to reach thresholds lower than about $2.10^{-2}$ ppm.volume and it may be necessary to determine the quantity of impurities which are found in a gas as traces, in lower quantities. This is particularly the case during the utilisation of silane in the manufacture of semi-conductors. This gas should indeed contain so called doping gas impurities, such as phosphine ($PH_3$), arsine ($AsH_3$) or hydrogen sulfide ($H_2S$). The effect of these impurities once incorporated into the semi-conductor should be controlled and maintained at a very specific level of concentration, which is very low, is exceeded. For example, it may be necessary to detect in silane traces of phosphine and arsine which are not in excess of $10^{-5}$ ppm.volume in order to be able to guarantee the quality of the silane used in the manufacture of semi-conductors.

SUMMARY OF INVENTION

It is therefore an object of the invention to decrease the detection thresholds of the chromatographic techniques in gas phase, in particular down to a level of detection of the order of $10^{-5}$ ppm.volume.

The process of determining the quantity of impurities in a gas by chromatography in gas phase according to the invention comprises the following steps:

Passing a gas loaded with impurities through a column filled with granular particles of an adsorbing product capable of adsorbing the impurities, said column being maintained at a temperature as low as possible without, however, reaching the liquefaction temperature of the gas; raising the temperature of the column and a passing flow of a carrier gas therethrough in order to desorb the impurities; carrying the desorbed impurities in the flow of a carrier gas, such as helium and passing the flow containing the desorbed impurities through column where preliminary chromatography in gas phase is undertaken selectively for each impurity in the gas to be analysed; sending the carrier gas at the outlet of the device for preliminary chromatography in a capillary column maintained at a temperature as low as possible; raising the temperature of the capillary column to desorb the impurities and carrying the impurities in a flow of neutral carrier gas; and, determining the quantity of impurities in a detector device, which can advantageously be a photo-ionisation detector.

The device for determining the quantity of impurities according to the invention comprises a device for cyrogenically trapping impurities which is provided with a column filled with granular particles of a product capable of adsorbing the impurities, refrigerating means capable of maintaining the column at low temperature during the passage of the gas loaded with impurities, and reheating means for ulterior desorption. The device also comprises a first chromatographic adsorber in gas phase which enables a preliminary analysis, a device for cyrogenically recentering impurities which is provided with a capillary column, refrigerating means capable of maintaining the column at a low temperature during the passage of a carrier gas which has gone through the first chromatographic adsorber, and desorption reheating means. The device finally comprises a second chromatographic adsorber in gas phase which is provided with a detection device.

The process for determining the quantity of impurities according to the invention is advantageously used for measuring the quantity of doping impurities in traces at a level of $10^{-5}$ ppm.volume in silane. For this purpose, the desired impurities are diluted in a multi-stage diluting bed, silane being added during the last stage of dilution, the impurities are determined by using the process of determining the quantity of impurities according to the invention and a retroaction is carried out on the bed of dilution to give the quantities of impurities desired.

BRIEF DESCRIPTION OF DRAWINGS

The invention will be better understood from a study of the detailed description of an embodiment described without any limitation and illustrated by means of the annexed drawings in which.

DESCRIPTION OF PREFERRED EMBODIMENTS

In the illustrated examples, the invention will be mainly described for determining the quantity of doping impurities such as phosphine, arsine and hydrogen sulfide in silane. It will of course be understood that the invention could apply without any modification to determining the quantities of impurities in another gas.

Figure 1:
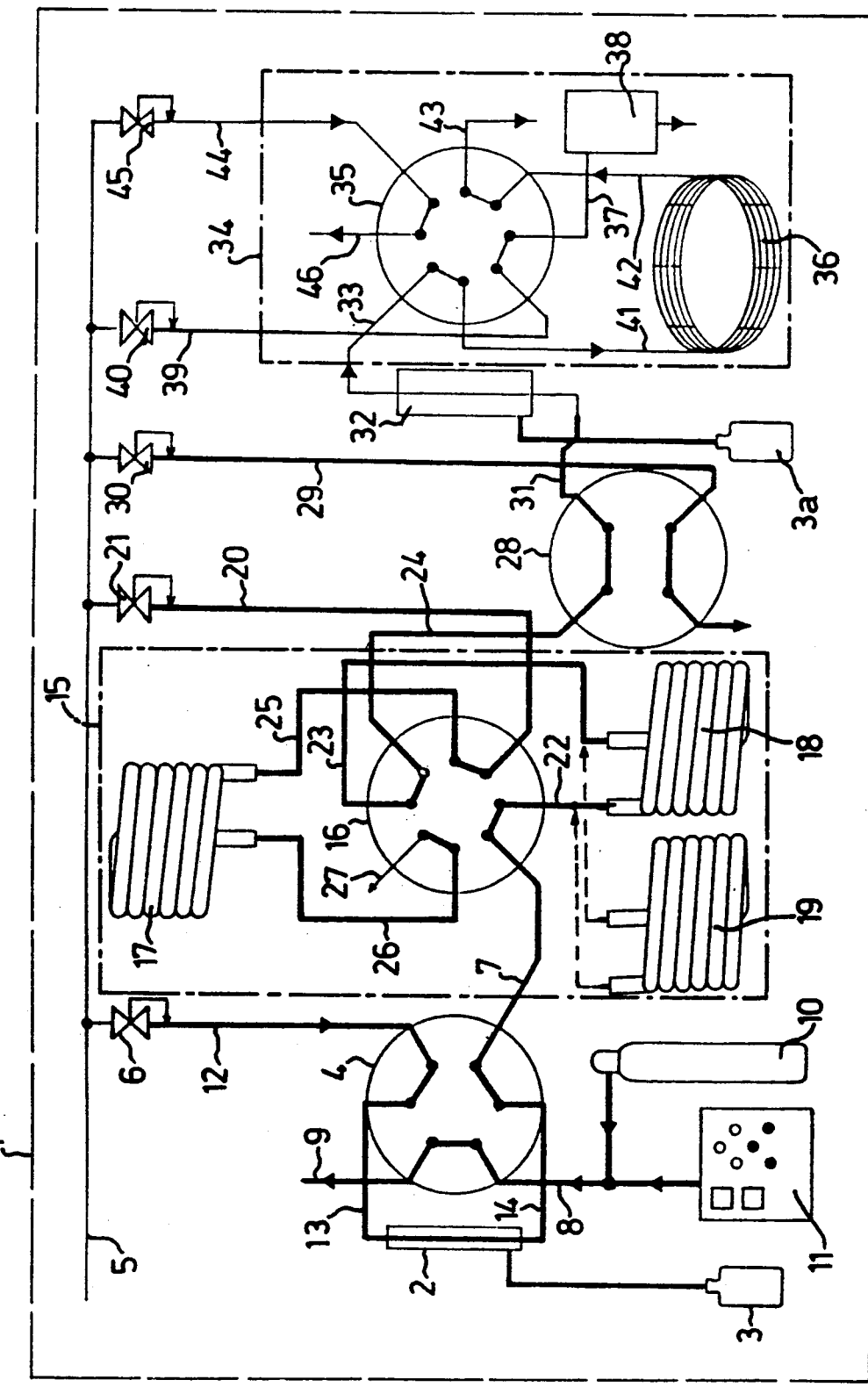
FIG. 1 is a schematic illustration of the main components of a device for determining the quantity of impurities according to the invention.

As illustrated in FIG. 1, the device for determining the quantity of impurities 1 by chromatography in gas phase according to the invention comprises a cryogenic trapping device 2 which can be supplied, for example, with liquid nitrogen originating from container 3. A first injection valve referred to as 4 in its entirety is schematically represented on the figure in the injection position for which a carrier gas such as helium originating from general channel 5 passes through the flow regulator 6 that goes through injection valve 4 before passing through cryogenic trap 2 and exiting via duct 7. In this position, the gas loaded with impurities and originating from duct 8 is sent into the atmosphere through exhaust duct 9. By way of example, there is additionally represented a bottle of a pure gas such as silane 10 and a system of calibration by dilution 11, which enables introduction of doping impurities such as phosphine, arsine and hydrogen sulfide into pure silane.

The cryogenic trapping device is kept at a low temperature but which low temperature is higher than the liquefaction temperature of the pure gas, silane.

This temperature is maintained as long as the valve remains in the position of injection where the carrier gas penetrates through duct 12 and therefore passes through the sampling loops 13, 14 comprising cryogenic trap 2. For adsorbing impurities in the cryogenic trapping device, the injection valve is placed in the reversed position. The gas mixture which passes through the sampling loop by penetrating through duct 14 into cryogenic trap 2 from which it exits via duct 13 before being sent into free air through duct 9. In this position, the carrier gas passes directly from inlet duct 12 to outlet duct 7.

The desorption of the impurities is then undertaken by raising the temperature of the trapping device 2 after having reset the valve 4 in the injection position as it is illustrated in FIG. 1.

The outlet duct 7 is connected at the inlet of a first chromatographic adsorber in the gas phase referenced as 15, and includes an eight way injection valve referenced as 16 and schematically illustrated in the same conditions as valve 4. In the illustrated example, the chromatographic adsorber 15 includes two coiled filling columns 17 and 18 capable of successively analysing two distinct impurities. A third coiled column 19 which can replace column 18 to enable the analysis and the detection of a third impurity has also been represented in FIG. 1. A carrier gas such as helium feeds the chromatographic adsorber 15 through a duct 20 which is connected to general duct 5 through flow regulator 21.

In the position of injection illustrated in FIG. 1, the neutral carrier gas, which carries the desorbed impurities originate from the cryogenic trap 2 through duct 7, passes first through column 18 via duct 22 and then comes back to valve 16 through duct 23 before exiting from the chromatographic adsorber 15 through duct 24. The carrier gas coming from duct 20 penetrates through duct 25 into column 17 before coming back to valve 16 and through duct 26 after which it is sent to free air through duct 27.

An analysis of the impurities carried out in the chromatographic adsorber 15, on columns 17, 18 and 19 enables obtaining a threshold of detection of the order of $2.10^{-4}$ to $10^{-4}$ ppm.volume because of the refrigerating concentration of the sample carried in the cryogenic trap 2. The detected peaks of the various impurities are however very flattened and it is recommended to proceed to a recentering of these peaks of impurities at the outlet of pre-columns 17, 18 and 19.

For this purpose, the outlet duct 24 is connected to a four way valve 28 which can be flushed with the carrier gas originating from duct 29 connected to general duct 5 by means of flow regulator 30. The outlet duct 31 coming from valve 28 is connected to the device for the cryogenic recentering of the impurities referenced as 32 in its entirety. This device is cooled with liquid nitrogen supplied from container 3a at a temperature as low as possible. It will be noted that contrary to what was the case with the cryogenic trapping device 2 wherein it was recommended not to reach the temperature of liquefaction of the pure gas such as silane, the problem is not the same in the device for cryogenic recentering 32 since the gas carrying the impurities is the carrier gas such as helium. It is therefore possible to still lower the temperature during the adsorption phase. The device for the cryogenic recentering of the impurities 32 is provided with a capillary column and its outlet 33 is connected to the inlet of a second chromatographic adsorber in gas phase referenced as 34 in its entirety. The second chromatographic adsorber 34 comprises an eight way injection valve 35. The chromatographic adsorber 34 also comprises a coiled capillary column 36 and a photo-ionisation detector 38 connected to the outlet 35. In the position illustrated in FIG. 1, the neutral carrier gas supplied through duct 39, including a flow regulator 40, passes through the injection valve 35 and is brought to detector 38. The temperature in the recentering device 32 is raised to produce the desorbtion. The carrier gas loaded with impurities originating from the cryogenic recentering device 32 passes through valve 35 then duct 41 and the capillary column 36 before returning through duct 42 and being sent to free air through duct 43. A flushing flow of the carrier gas from duct 44 including a flow regulator 45 is also sent to free air through duct 46 after having passed through injection valve 35.

The second chromatographic adsorber enables obtaining an analysis with a precision of $10^{-5}$ ppm.volume.

Figure 2:
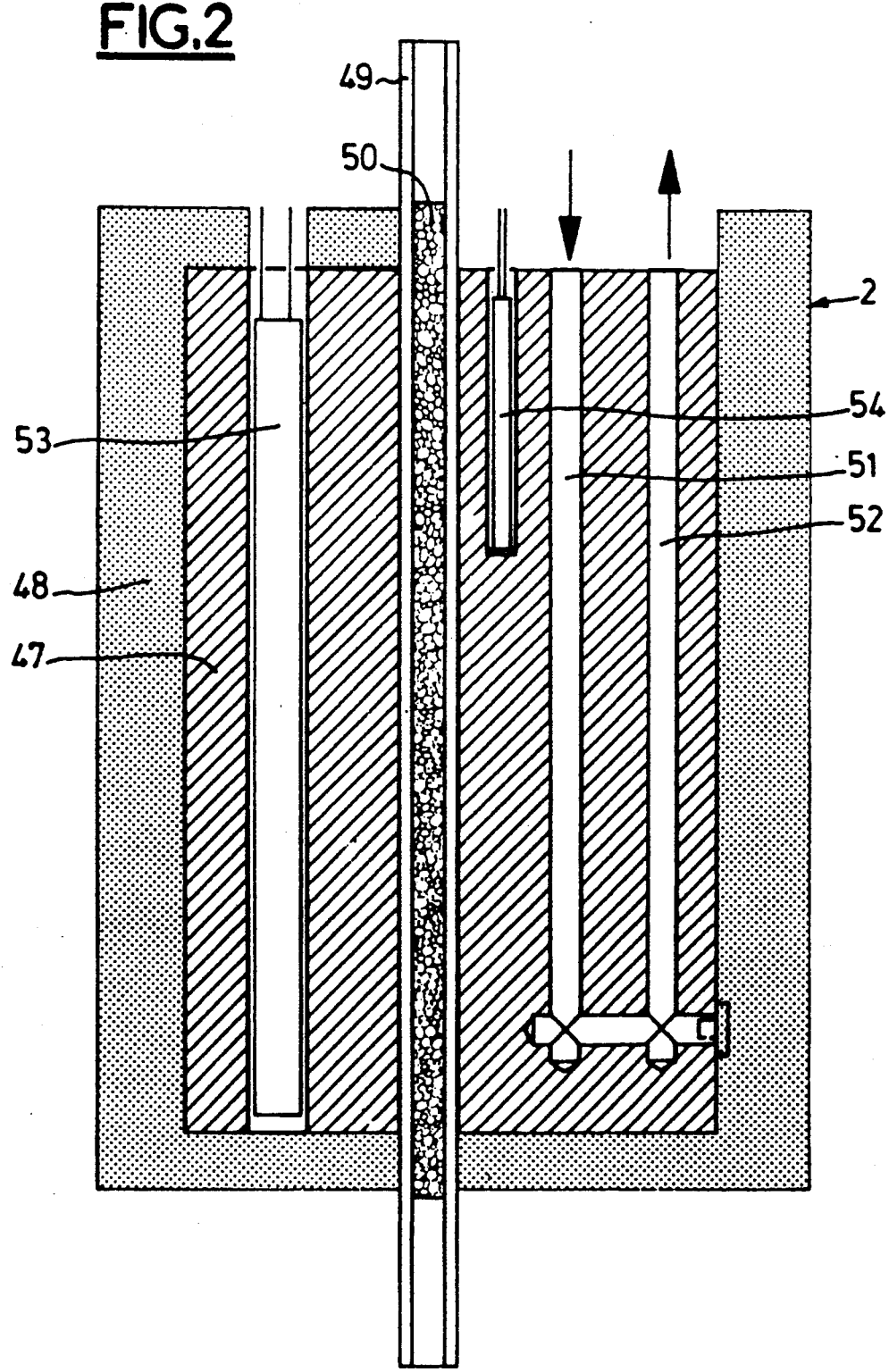
FIG. 2 is a schematic cross-section view of the cryogenic trapping device used in the invention.

FIG. 2 is a schematic illustration of an embodiment of the device for cryogenic trapping 2. The latter comprises a central body 47 surrounded by an insulating material 48. A rectilinear sampling tube 49 constituting a filling column 50 of granular particles of a product capable of adsorbing the impurities which are intended to be analysed passes through the central body 47 substantially axially thereof. The refrigerating fluid made for example of liquid nitrogen penetrates into the inlet channel 51 and exits through outlet channel 52 after having passed along the entire height of the body 47 to ensure its cooling as well as that of the sampling tube 49. A heating plug 53 also disposed along the entire height of body 47 enables to warm the sampling tube to carry out desorption. A temperature measuring probe 54 enables control of the temperature and maintains the sample tube at a low temperature during the phase of adsorption of the impurities.

Figure 3:
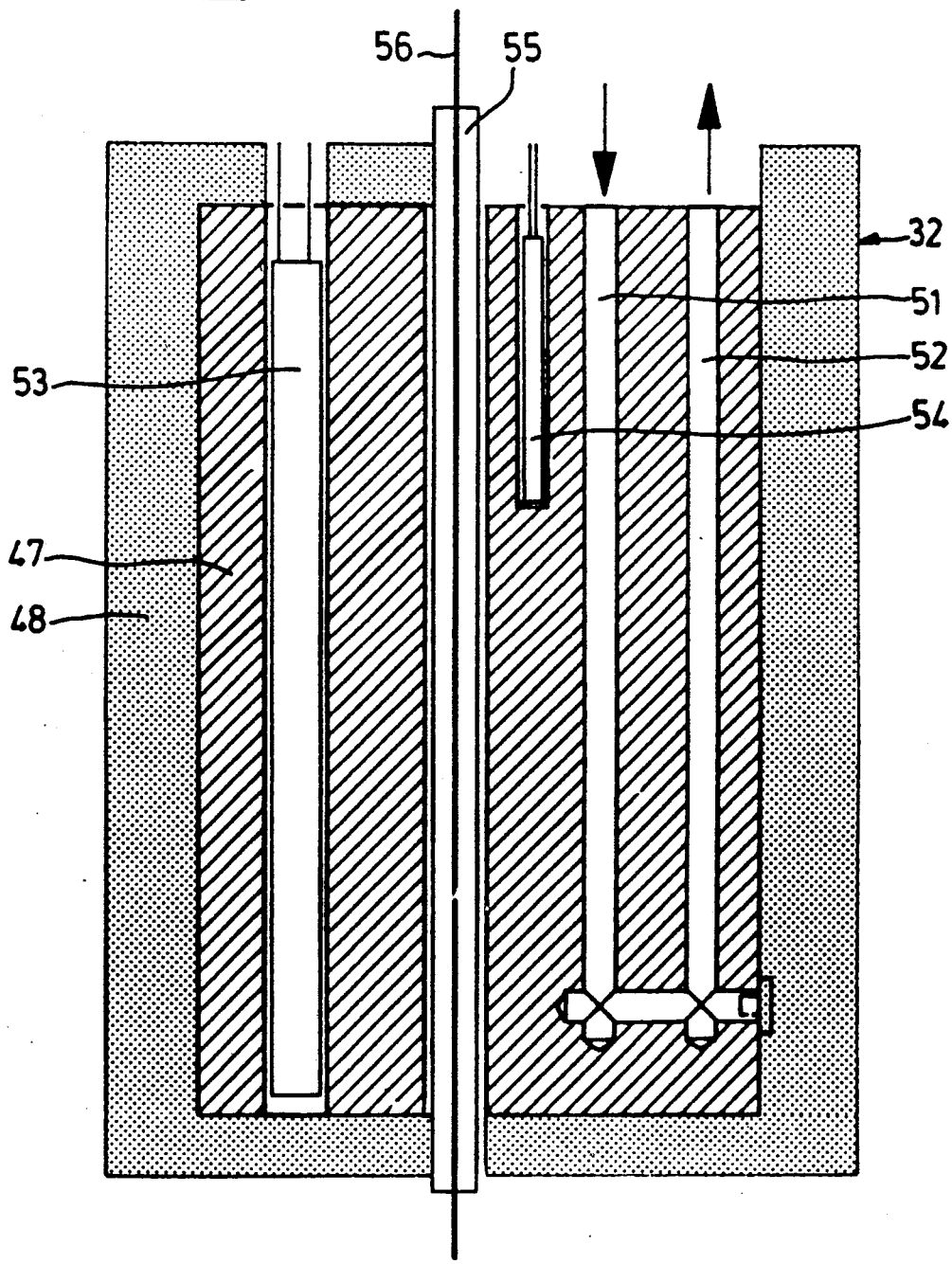
FIG. 3 is a schematic cross-section view of the cryogenic recentering device used in the present invention.

FIG. 3 illustrates the device of cryogenic recentering 32. The latter has the same general structure as trapping device 2. As a matter of fact, it includes a similar central body which is also referenced as 47 and is made of an insulating material 48 and cooling channels 51, 52. There is a measuring probe 54 and a heating plug 53 for desorption. The difference is in the replacement of the sampling tube 49 by a central tube 55 having a capillary bore enabling mounting therein, a rectilinear capillary column 56 which extends along the height of body 47.

Figure 4:
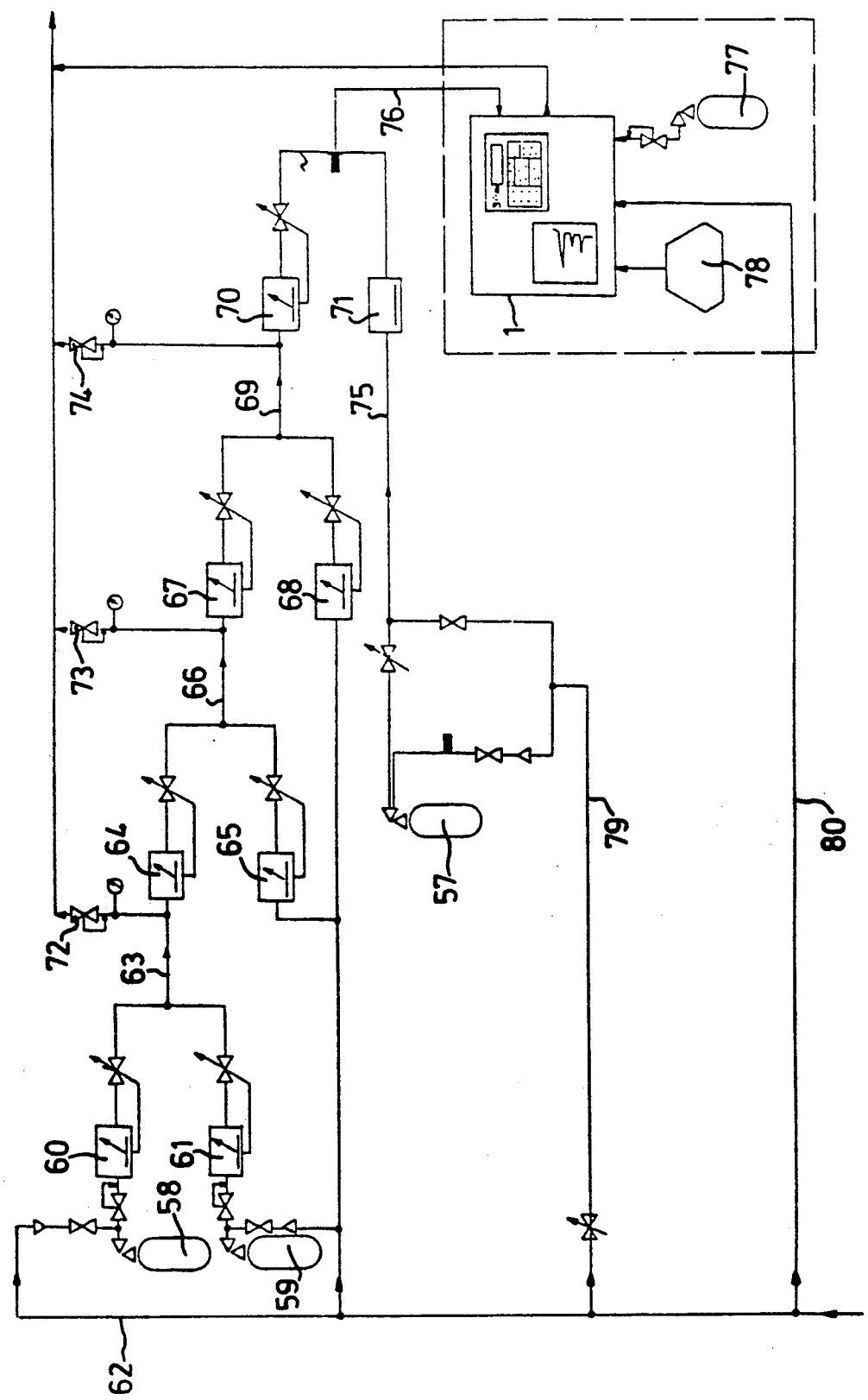
FIG. 4 is a schematic illustration of a system of measuring the quantity of impurities in a gas such as silane at very low concentration.

FIG. 4 illustrates an apparatus for measuring the quantity of impurities. By way of example, there is introduced here pure silane from container 57, and doping impurities consisting of phosphine, arsine and hydrogen sulfide. For this purpose, container 58 contains a mixture of nitrogen, phosphine and arsine and container 59 contains a mixture of nitrogen and hydrogen sulfide. A first stage of dilution in nitrogen comprises the two flow mass regulators 60 and 61 whose inlets are respectively connected to containers 58 and 59 as well as to main hydrogen channel 62 while their common outlets 63 feed a second stage of dilution of nitrogen. The second stage of dilution also comprises two mass flow regulators 64 and 65. The outlet 66 of the second stage is connected to the third stage of dilution in nitrogen which comprises the two mass flow regulators 67 and 68. Their common outlet 69 is connected to the fourth stage carrying out the final dilution in silane and including the two mass flow regulators 70 and 71. It will be noted that the mass flow regulators 64, 67 and 70 are also connected to dischargers 72, 73 and 74. The silane from container 57 is brought through duct 76 to the fourth stage of dilution by means of regulator 71. The silane so loaded with impurities is brought through duct 76 through the chromatographic measuring device 1 which on the other hand receives the carrier gas contained in the container 77 and can be supplied, for refrigerating its elements, with liquid nitrogen contained in the container 78.

The circuit is completed by means of nitrogen flushing channels 79 and 80.

The measure of the quantity and the analysis of the impurities carried out with the device for determining the quantities of impurities 1 enables retroacting on the stages of dilution by means not illustrated in the figure, so as to finally give a mixture of silane of which the phosphine, arsine and hydrogen sulfide impurities are perfectly determined at the level of $10^{-5}$ ppm.volume.

We claim:

1. A method of determining trace levels of at least one gaseous impurity loaded in a pure gas having a first liquefaction temperature, comprising:
    cooling with a cryogen a first column filled with a first adsorbent capable of adsorbing said at least one impurity at a first low temperature greater than said first liquefaction temperature;
    passing said gas containing said at least one impurity through said first column at said first low temperature to adsorb said at least one impurity;
    raising the temperature of the first column while passing through said first column a carrier gas having a second liquefaction temperature lower than said first liquefaction temperature to desorb said at least one impurity;
    passing said carrier gas carrying said desorbed impurity to a first chromatographic adsorber;
    conducting a first gas phase chromatography analysis to analyze said at least one impurity with a first level of accuracy;
    passing the carrier gas through the first chromatographic adsorber to desorb said at least one impurity;
    cooling with a cryogen a second column filled with a second adsorbent capable of adsorbing said at least one impurity at a second low temperature lower than said first liquefaction temperature and greater than said second liquefaction temperature;
    passing said carrier gas carrying said desorbed impurity through the second column to adsorb said impurity;
    raising the temperature of the second column while passing therethrough the carrier gas to desorb said impurity;
    passing said carrier gas carrying said desorbed impurity to a second chromatographic adsorber having a detection device; and
    conducting a second gas phase chromatography analysis to analyze said impurity with a second level of accuracy higher than said first level of accuracy of about $10^{-5}$ ppmv.

2. The method of claim 1, wherein the second column comprises a capillary column.

3. The method of claim 2, wherein the second chromatographic adsorber comprises at least one coiled capillary column.

4. The method of claim 2, wherein the cryogen is liquid nitrogen and the carrier gas is helium.

5. The method of claim 2, wherein said impurity is a doping component for doping a semi-conductor material.

6. The method of claim 5, wherein said gas is silane and said gaseous impurity is selected from the group consisting of said phosphine, arsine and hydrogen sulfide.

7. The method of claim 5, further comprising the steps of:
    elaborating said gas containing said impurity to be analyzed by diluting said impurity in said gas in a multi-stage dilution station fed with said gas in a pure state and modifying operation of said dilution station with a second analysis to obtain trace levels of said impurity in said gas.

* * * * *